United States Patent
Audousset et al.

(10) Patent No.: US 6,440,176 B2
(45) Date of Patent: *Aug. 27, 2002

(54) OXIDATION DYEING COMPOSITION FOR KERATINOUS FIBERS CONTAINING A PARAPHENYLENEDIAMINE DERIVATIVE AND DYEING METHOD USING SAME

(75) Inventors: Marie-Pascale Audousset, Asniéres; Jean Cotteret, Verneuil sur Seine, both of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/297,686

(22) PCT Filed: Oct. 23, 1997

(86) PCT No.: PCT/FR97/01901

§ 371 (c)(1), (2), (4) Date: Jun. 3, 1999

(87) PCT Pub. No.: WO98/19662

PCT Pub. Date: May 14, 1998

(30) Foreign Application Priority Data

Nov. 7, 1996 (FR) .............................. 96/13600

(51) Int. Cl.⁷ ................................ A61K 7/13
(52) U.S. Cl. .................. 8/407; 8/408; 8/410; 8/412; 8/416; 8/421; 8/424
(58) Field of Search .................. 8/407, 408, 410, 8/412, 416, 421, 424

(56) References Cited

U.S. PATENT DOCUMENTS

| 4,152,112 A | 5/1979 | Bugaut et al. | 8/410 |
| 4,311,478 A | 1/1982 | Bugaut et al. | 8/407 |
| 4,888,025 A | 12/1989 | Bugaut et al. | |
| 5,514,188 A | 5/1996 | Cotteret et al. | 8/412 |
| 5,518,507 A | 5/1996 | Audousset et al. | 8/411 |
| 5,529,584 A | 6/1996 | Audousset et al. | 8/412 |
| 5,538,516 A | 7/1996 | Audousset et al. | 8/412 |
| 5,567,421 A | 10/1996 | Cotteret et al. | 8/408 |
| 5,863,300 A | 1/1999 | Audousset et al. | 8/411 |

FOREIGN PATENT DOCUMENTS

| FR | 2 364 888 | 4/1978 |
| FR | 2 586 913 | 3/1987 |

OTHER PUBLICATIONS

Zviak, The Science of Hair Care, pp. 266, 284 1986.*
English language Derwent Abstract of FR 2 586 913, Mar. 1987.

* cited by examiner

*Primary Examiner*—Margaret Einsmann
(74) *Attorney, Agent, or Firm*—Finnegan, Henderson, Farabow, Garrett, & Dunner, L.L.P.

(57) ABSTRACT

A composition for the oxidation dyeing of keratinous fibers such as hair, comprises at least one para-phenylenediamine derivative as oxidation base, in combination with at least one coupler of meta-aminophenol or meta-diphenol type, and the dyeing process employing this composition.

37 Claims, No Drawings

OXIDATION DYEING COMPOSITION FOR KERATINOUS FIBERS CONTAINING A PARAPHENYLENEDIAMINE DERIVATIVE AND DYEING METHOD USING SAME

The subject-matter of the invention is a composition for the oxidation dyeing of keratinous fibres, in particular of human keratinous fibres, such as hair, comprising at least one suitably selected para-phenylenediamine derivative as oxidation base, in combination with at least one suitably selected coupler of meta-aminophenol or meta-diphenol type, and the dyeing process employing this composition.

It is known to dye keratinous fibres and in particular human hair with dyeing compositions comprising oxidation dye precursors, in particular ortho- or para-phenylenediamines or ortho- or para-aminophenols, generally known as oxidation bases. Oxidation dye precursors or oxidation bases are colourless or weakly coloured compounds which, in combination with oxidizing substances, can give rise by an oxidative coupling process to coloured and colouring compounds.

It is also known that the shades obtained with these oxidation bases can be varied by combining them with couplers or colouring modifiers, the latter being chosen in particular from aromatic meta-diamines, meta-aminophenols or meta-diphenols.

The variety of the molecules employed as oxidation bases and couplers makes it possible to obtain a rich palette of colours.

The so-called "permanent" colouring obtained by virtue of these oxidation dyes has, however, to satisfy a certain number of requirements. Thus, it must be without disadvantage toxicologically and it must make it possible to obtain shades with the desired intensity and behave well in the face of external agents (light, bad weather, washing, permanent waving, perspiration or rubbing).

Provision has already been made, in particular in French Patent Application FR-A-2 364 888, for compositions for the oxidation dyeing of keratinous fibres comprising, as oxidation base, para-phenylenediamines substituted in the 2 position, such as, for example, 2-(β-mesylaminoethyloxy)-para-phenylenediamine, optionally in combination with one or more couplers of meta-aminophenol, such as, for example, 5-amino-2-methylphenol, meta-phenylenediamine or meta-diphenol type, in order to obtain, in oxidizing alkaline medium, colourings with blue shades which are more or less purple, these being very luminous. The colourings obtained with these compositions are not, however, entirely satisfactory, in particular as regards the behaviour of these colourings with respect to various attacks which hair may be subjected to and in particular with respect to perspiration and permanent waving.

The present invention is targeted at providing novel compositions for the oxidation dyeing of keratinous fibres and in particular of human keratinous fibres, such as hair, which exhibit very good dyeing properties.

Thus, the Applicant Company has now just discovered that it is possible to obtain novel dyes which are particularly resistant and which generate intense colourings by combining:

at least one para-phenylenediamine derivative of formula (I) defined below and/or one of its addition salts with an acid,
at least coupler of formula (II) defined below and/or one of its addition salts with an acid.

This discovery is at the basis of the present invention.

The first subject-matter of the invention is therefore a composition for the oxidation dyeing of keratinous fibres and in particular of human keratinous fibres, such as hair, characterized in that it comprises, in a medium appropriate for dyeing:

at least one oxidation base chosen from para-phenylenediamine derivatives of following formula (I) and their addition salts with an acid:

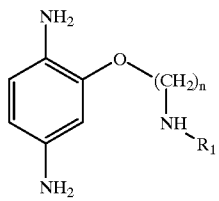

(I)

in which:
R$_1$ represents a hydrogen atom or a mesyl, carbamoyl or acetyl radical,
n is an integer between 1 and 4 inclusive;
at least one coupler chosen from compounds of following formula (II) and their addition salts with an acid:

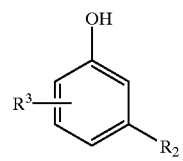

(II)

in which:
R$_2$ represents a hydroxyl radical or an NHR$_4$ group where R$_4$ denotes a hydrogen atom or a C$_1$–C$_4$ alkyl, C$_1$–C$_4$ monohydroxyalkyl or C$_2$–C$_4$ polyhydroxyalkyl radical,
R$_3$ represents a hydrogen atom, a C$_1$–C$_4$ alkyl or C$_1$–C$_4$ alkoxy radical or a halogen atom chosen from chlorine, bromine and fluorine;
it being understood that, when n=2, when R$_1$ represents a mesyl radical, when R$_3$ represents a methyl radical in the 6 position and when R$_2$ represents an NHR$_4$ group, then R$_4$ is other than a hydrogen atom.

The colourings obtained with the above compositions exhibit a good dyeing power and excellent properties of resistance both with respect to atmospheric agents, such as light and bad weather, and with respect to perspiration and various treatments which hair can be subjected to (shampoos, permanent deformations).

Another subject-matter of the invention is a process for the oxidation dyeing of keratinous fibres employing this composition.

The addition salts with an acid which can be used in the context of the dyeing compositions of the invention can in particular be chosen from hydrochlorides, hydrobromides, sulphates and tartrates.

Mention may more particularly be made, among the para-phenylenediamine derivatives of above formula (I), of 2-(β-mesylaminoethyloxy)-para-phenylenediamine, 2-(β-ureidoethyloxy)-para-phenylenediamine, 2-(β-acetylaminoethyloxy)-para-phenylenediamine, 2-(β-aminoethyloxy)-para-phenylenediamine and their addition salts with an acid.

Mention may more particularly be made, among the couplers of above formula (II), of meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(γ-hydroxypropyl)amino-2-methylphenol, 1,3-dihydroxybenzene, 2-methyl-1,3-dihydroxybenzene, 4-chloro-1,3-dihydroxybenzene and their addition salts with an acid.

The para-phenylenediamine derivative or derivatives of formula (I) in accordance with the invention and/or its or their addition salts with an acid preferably represent from 0.0005 to 10% by weight approximately of the total weight of the dyeing composition and more preferably still from 0.05 to 7% by weight approximately.

The coupler or couplers of formula (II) in accordance with the invention and/or its or their addition salts with an acid preferably represent from 0.0001 to 5% by weight approximately of the total weight of the dyeing composition and more preferably still from 0.005 to 3% by weight approximately.

The medium appropriate for dyeing (or vehicle) is generally composed of water or of a mixture of water and of at least one organic solvent, in order to dissolve the compounds which would not be sufficiently soluble in water. Mention may be made, for example, as organic solvent, of lower $C_1$–$C_4$ alkanols, such as ethanol and isopropanol; glycerol; glycols and glycol ethers, such as 2-butoxyethanol, propylene glycol, diethylene glycol monoethyl ether and diethylene glycol monomethyl ether, and aromatic alcohols, such as benzyl alcohol or phenoxyethanol, the analogous products and their mixtures.

The solvents can be present in proportions preferably of between 1 and 40% by weight approximately with respect to the total weight of the dyeing composition and more preferably still between 5 and 30% by weight approximately.

The pH of the dyeing composition as defined above is generally between 5 and 12 approximately. It can be adjusted to the desired value by means of acidifying or basifying agents commonly used in dyeing keratinous fibres.

Mention may be made, among acidifying agents, by way of examples, of inorganic or organic acids, such as hydrochloric acid, orthophosphoric acid, carboxylic acids, such as tartaric acid, citric acid or lactic acid, or sulphonic acids.

Mention may be made, among basifying agents, by way of examples, of aqueous ammonia, alkaline carbonates, alkanolamines, such as mono-, di- and triethanolamines, and their derivatives, sodium hydroxide, potassium hydroxide and the compounds of following formula (III):

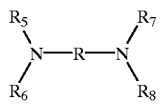

(III)

in which R is a propylene residue optionally substituted by a hydroxyl group or a $C_1$–$C_4$ alkyl radical; and $R_5$, $R_6$, $R_7$ and $R_8$, which are identical or different, represent a hydrogen atom or a $C_1$–C4 alkyl or $C_1$–$C_4$ hydroxyalkyl radical.

The dyeing composition in accordance with the invention can also comprise, in addition to the dyes defined above, other oxidation bases other than the para-phenylenediamine derivatives of formula (I) in accordance with the invention and/or other couplers other than the couplers of formula (II) in accordance with the invention and/or direct dyes, in particular for modifying the shades or enriching them with highlights.

The dyeing composition according to the invention can also include various adjuvants conventionally used in hair dyeing compositions, such as anionic, cationic, non-ionic or amphoteric surface-active agents or their mixtures, anionic, cationic, non-ionic or amphoteric polymers or their mixtures, inorganic or organic thickening agents, antioxidizing agents, penetration agents, sequestering agents, fragrances, buffers, dispersing agents, conditioning agents, such as, for example, silicones, film-forming agents, preserving agents or opacifying agents.

Of course, a person skilled in the art will take care to choose the optional additional compound or compounds mentioned above so that the advantageous properties intrinsically attached to the dyeing composition according to the invention are not, or not substantially, detrimentally affected by the envisaged addition or additions.

The dyeing composition according to the invention can be provided in various forms, such as in the form of liquids, creams or gels, or in any other form appropriate for carrying out dyeing of keratinous fibres and in particular of human hair.

Another subject-matter of the invention is a process for dyeing keratinous fibres and in particular human keratinous fibres, such as hair, employing the dyeing composition as defined above.

According to this process, the dyeing composition as defined above is applied to the fibres to be coloured, the colour being developed at acidic, neutral or alkaline pH using an oxidizing agent which is added only at the time of use to the dyeing composition or which is present in an oxidizing composition applied simultaneously or sequentially in a separate fashion.

According to a preferred embodiment of the invention, the pH resulting from the mixing of the dyeing composition and of the oxidizing composition is between 5 and 12 approximately.

According to a particularly preferred embodiment of the dyeing process according to the invention, the dyeing composition described above is mixed, at the time of use, with an oxidizing composition comprising, in a medium appropriate for dyeing, at least one oxidizing agent present in an amount sufficient to develop a colouring. The mixture obtained is subsequently applied to the keratinous fibres and is left to stand for 3 to 40 minutes approximately, preferably 5 to 30 minutes approximately, after which the hair is rinsed, washed with a shampoo, rinsed again and dried.

The oxidizing agent present in the oxidizing composition as defined above can be chosen from oxidizing agents conventionally used for the oxidation dyeing of keratinous fibres and among which may be mentioned hydrogen peroxide, urea hydrogen peroxide, alkali metal bromates, or persalts, such as perborates and persulphates. Hydrogen peroxide is particularly preferred.

The pH of the oxidizing composition including the oxidizing agent as defined above is such that, after mixing with the dyeing composition, the pH of the resulting composition applied to keratinous fibres preferably varies between 2 and 12 approximately and more preferably still between 5 and 11. It is adjusted to the desired value by means of acidifying or basifying agents commonly used in dyeing keratinous fibres and as defined above.

The oxidizing composition as defined above can also include various adjuvants conventionally used in hair dyeing compositions and as defined above.

The composition which is finally applied to keratinous fibres can be provided in various forms, such as in the form of liquids, creams or gels, or in any other form appropriate for carrying out dyeing of keratinous fibres and in particular of human hair.

Another subject-matter of the invention is a dyeing multi-compartment device or kit or any other packaging system with several compartments, a first compartment of which includes the dyeing composition as defined above and a second compartment of which includes the oxidizing composition as defined above. These devices can be equipped with a means allowing the desired mixture to be deposited on the hair, such as the devices disclosed in Patent FR-A-2,586,913 on behalf of the Applicant Company.

The examples which follow are intended to illustrate the invention without, for all that, limiting the scope thereof.

EXAMPLES

Comparative Examples 1 to 4

The following dyeing compositions were prepared (contents in grams):

| EXAMPLE | 1 | 2 (*) | 3 | 4 (*) |
|---|---|---|---|---|
| 2-(β-Acetylamino-ethyloxy)-para-phenylenediamine dihydrochloride (oxidation base in accordance with the invention) | 0.845 | 0.845 | | |
| 2-(β-Aminoethyloxy)-para-phenylenediamine trihydrochloride (oxidation base in accordance with the invention) | | | 0.83 | 0.83 |
| 5-N-(β-Hydroxyethyl)amino-2-methoxyphenol (coupler in accordance with the invention) | 0.54 | | 0.54 | |
| 2-Methoxy-5-(carbethoxyamino)phenol (coupler not forming part of the invention) | | 0.63 | | |
| 5-Acetylamino-2-methoxyphenol (coupler not forming part of the invention) | | | | 0.54 |
| Common dyeing vehicle () | () | () | () | (**) |
| Water, q.s. for | 100 g | 100 g | 100 g | 100 g |

(*): example not forming part of the invention
(**): Common dyeing vehicle:

| | |
|---|---|
| 96° Ethanol | 18.0 g |
| Pentasodium salt of diethylenetriaminepentaacetic acid | 1.08 g |
| Sodium metabisulphite as an aqueous solution comprising 35% of A.M. | 0.58 g |
| Aqueous ammonia comprising 20% of $NH_3$ | 10.0 g |

It is important to note that each dyeing composition comprises the same molar amount of coupler and the same molar amount of oxidation base, namely $3 \times 10^{-3}$ mol.

At the time of use, each dyeing composition was mixed with an equal amount of an oxidizing composition consisting of a 20-volume aqueous hydrogen peroxide solution (6% by weight) exhibiting a pH of approximately 3.

Each mixture obtained was applied for 30 minutes to two batches of locks of natural grey hair comprising 90% of white hairs (Batch A and Batch B). The locks of hair were subsequently rinsed, washed with a standard shampoo and then dried.

The colour of the locks (Batch A and Batch B) was subsequently evaluated in the Munsell system by means of a CM 2002 Minolta calorimeter (ASTM Standard D 1535-68).

According to the Munsell notation, a colour is defined by the expression H V/C, in which the three parameters respectively denote the tint or Hue (H), the intensity or Value (V) and the purity or Chromaticity (C), the oblique stroke in this expression being simply a convention and not indicating a ratio.

Resistance to Permanent Waving

The dyed locks of hair from Batch A were subjected to a test of resistance to permanent waving.

To do this, the locks of hair from Batch A were immersed for 10 minutes in a reducing solution in a ratio of 2 g of the following reducing solution per lock weighing 1 g:

| Reducing solution | |
|---|---|
| Thioglycolic acid | 6.7 g |
| Diammonium dithioglycolate at 48% in water | 5.0 g |
| Basifying agent, q.s. | pH = 7.9 |
| Demineralized water, q.s. for | 100.0 g |

After rinsing, the locks of hair from Batch A were immersed for 5 minutes in an oxidizing solution (consisting of an 8-volume hydrogen peroxide solution with a pH of 3) in the ratio of 2 g of oxidizing solution per lock weighing 1 g.

The locks were subsequently rinsed with water and then dried for 1 hour at 60° C., The colour of the locks of hair from Batch A was subsequently evaluated again in the Munsell system by means of a CM 2002 Minolta calorimeter.

The difference between the colour of the lock before the permanent waving and the colour of the lock after the permanent waving was calculated by applying the Nickerson formula:

$$\Delta E = 0.4 Co \Delta H + 6 \Delta V + 3 \Delta C$$

as described, for example, in "Couleur, Industrie et Technique" [Colour, Industry and Technology], pages 14–17, Vol. No. 5, 1978.

In this formula, $\Delta E$ represents the difference in colour between two locks, $\Delta H$, $\Delta V$ and $\Delta C$ represent the variation in absolute value of the parameters H, V and C, and Co represents the purity of the lock with respect to which it is desired to evaluate the difference in colour.

The deterioration in colour ($\Delta E$) increases as the figure shown increases.

The results are given in Table I below:

| EX-AM-PLE | Colour of the hair before the permanent waving | Colour of the hair after the permanent waving | Deterioration in the colour | | | |
|---|---|---|---|---|---|---|
| | | | $\Delta H$ | $\Delta V$ | $\Delta C$ | $\Delta E$ |
| 1 | 9.7 YR 3.8/1.1 | 0.2 Y 4.5/1.5 | 0.5 | 0.7 | 0.4 | 5.6 |
| 2 (*) | 9.6 PB 2.9/2.1 | 8.6 P 4.0/0.6 | 9.0 | 1.1 | 1.5 | 18.7 |
| 3 | 1.2 Y 2.7/0.6 | 9.9 YR 3.2/1.0 | 1.3 | 0.5 | 0.4 | 4.5 |
| 4 (*) | 6.3 PB 2.6/0.9 | 6.4 YR 3.5/0.7 | 40.1 | 0.9 | 0.2 | 20.4 |

(*): Example not forming part of the invention.

These results show that the compositions 1 and 3 in accordance with the invention, that is to say comprising the combination of a para-phenylenediamine derivative of formula (I) and of a coupler of formula (II), result in colourings which withstand permanent waving much better than the colourings obtained with the compositions 2 and 4, which do not form part of the invention because they contain the combination of a para-phenylenediamine derivative of formula (I) in accordance with the invention and of a coupler not corresponding to the formula (II) of the invention. These compositions 2 and 4 of the prior art are disclosed, for example, in Patent Application FR-A-2,364,888.

Resistance to Perspiration

The dyed locks of hair from Batch B were subjected to a test of resistance to perspiration.

To do this, the locks of hair from Batch B were immersed in a crystallizing dish, covered with a watch-glass, containing a synthetic sweat solution with the following composition:

| | |
|---|---|
| NaCl | 1 g |
| Potassium hydrogenphosphate | 0.1 g |
| Histidine | 0.025 g |
| Lactic acid q.s. | pH 3.2 |
| Distilled water, q.s. for | 100 g |

The locks of dyed hair from Batch B were left standing in this synthetic sweat solution for 48 hours at 37° C. The locks were subsequently rinsed and then dried.

The colour of the locks from Batch B was subsequently evaluated again in the Munsell system by means of a CM 2002 Minolta calorimeter, so as to determine the deterioration in the colourings after this test of resistance to perspiration.

The difference in colour between two locks (in this instance, before and after the treatment simulating perspiration) was calculated by applying the Nickerson formula as described above.

The results are given in Table II below:

| EX-AM-PLE | Colour of the hair before perspiration | | Colour of the hair after the perspiration | | Deterioration in the colour | | | |
|---|---|---|---|---|---|---|---|---|
| | | | | | ΔH | ΔV | ΔC | ΔE |
| 1 | 9.7 YR | 3.8/1.1 | 1.3 Y | 4.6/0.9 | 1.6 | 0.8 | 0.2 | 6.1 |
| 2 (*) | 9.6 PB | 2.9/2.1 | 6.0 P | 3.9/1.1 | 6.4 | 1.0 | 1.0 | 14.4 |
| 3 | 1.2 Y | 2.7/0.6 | 8.2 YR | 3.8/0.8 | 3.0 | 1.1 | 0.2 | 7.9 |
| 4 (*) | 6.3 PB | 2.6/0.9 | 2.8 YR | 3.8/0.7 | 36.5 | 1.2 | 0.3 | 21.2 |

(*): Example not forming part of the invention.

These results show that the compositions 1 and 3 in accordance with the invention, that is to say comprising the combination of a para-phenylenediamine derivative of formula (I) and of a coupler of formula (II), result in colourings which withstand perspiration much better than the colourings obtained with the compositions 2 and 4, which do not form part of the invention because they contain the combination of a para-phenylenediamine derivative of formula (I) in accordance with the invention and of a coupler not corresponding to the formula (II) of the invention. These compositions 2 and 4 of the prior art are disclosed, for example, in Patent Application FR-A-2,364,888.

Dyeing Examples 5 to 12

The following dyeing compositions in accordance with the invention were prepared (contents in grams):

| EXAMPLE | 5 | 6 | 7 | 9 | 10 | 11 |
|---|---|---|---|---|---|---|
| 2-(β-Acetylaminoethyloxy)-para-phenylenediamine dihydrochloride (Oxidation base) | 0.417 | 0.417 | 0.417 | — | — | — |
| 2-(β-Aminoethyloxy)-para-phenylenediamine trihydrochloride (Oxidation base) | — | — | — | 0.415 | 0.415 | 0.415 |
| Resorcinol (Coupler) | 0.33 | — | — | 0.33 | — | — |
| meta-Aminophenol (Coupler) | — | 0.327 | — | — | 0.327 | — |
| 5-N-(β-Hydroxyethyl) amino-2-methylphenol (Coupler) | — | — | 0.50 | — | — | 0.50 |
| 2, 4-Diaminophenoxyethanol dihydrochloride (Coupler) | — | — | — | — | — | — |
| Common dyeing vehicle (*) | (*) | (*) | (*) | (*) | (*) | (***) |
| Water, q.s. for | 100 g | 100 g | 100 g | 100 g | 100 g | 100 g |

| (***) Common dyeing vehicle: | |
|---|---|
| Oleyl alcohol polyglycerolated with 2 mol of glycerol | 4.0 g |
| Oleyl alcohol polyglycerolated with 4 mol of glycerol comprising 78% of active material (A.M.) | 5.69 g A.M. |
| Oleic acid | 3.0 g |
| Oleylamine with 2 mol of ethylene oxide, sold under the tradename Ethomeen O12 by the company Akzo | 7.0 g |
| Diethylaminopropyl laurylaminosuccinamate, sodium salt, comprising 55% of A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite as an aqueous solution comprising 35% of A.M. | 0.455 g A.M. |
| Ammonium acetate | 0.8 g |
| Antioxidizing agent, sequestering agent | q.s. |
| Fragrance, preserving agent | q.s. |
| Aqueous ammonia comprising 20% of $NH_3$ | 10.0 g |

At the time of use, each dye composition was mixed with an equal amount of an oxidizing composition consisting of a 20-volume aqueous hydrogen peroxide solution (6% by weight) exhibiting a pH of approximately 3.

Each mixture obtained exhibited a pH of approximately 10.2 and was applied for 30 minutes to locks of natural or permed grey hair comprising 90% of white hairs. The locks of hair were subsequently rinsed, washed with a standard shampoo and then dried.

The locks of hair were dyed in the shades which appear in the table below:

| EXAMPLE | SHADE OF NATURAL HAIR | SHADE ON PERMED HAIR |
|---|---|---|
| 5 | Ash beige | Slightly iridescent natural golden |
| 6 | Ash deep-purple | Ash deep-purple |
| 7 | Slightly iridescent ash deep-purple | Ash deep-purple |
| 9 | Matt natural grey | Matt natural grey |
| 10 | Matt natural grey | Matt natural grey |
| 11 | Slightly purplish ashen | Purplish ashen |

What is claimed is:
1. A composition for the oxidation dyeing of keratinous fibres, wherein said composition comprises, in a medium appropriate for dyeing:

at least one oxidation base chosen from para-phenylenediamines of formula (I) and acid addition salts thereof:

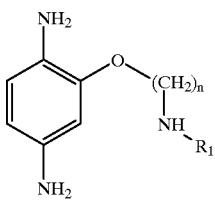

(I)

in which:
R₁ is chosen from a hydrogen atom, mesyl radicals, carbamoyl radicals, and acetyl radicals,
n is an integer ranging from 1 to 4; and
at least one coupler chosen from compounds of formula (II) and acid addition salts thereof:

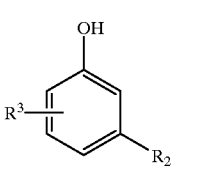

(II)

in which:
$R_2$ is chosen from a hydroxyl radical and $NHR_4$ groups where $R_4$ is chosen from a hydrogen atom, $C_1$–$C_4$ alkyl radicals, $C_1$–$C_4$ monohydroxyalkyl radicals, and $C_2$–$C_4$ polyhydroxyalkyl radicals,
$R_3$ is chosen from a hydrogen atom, $C_1$–$C_4$ alkyl radicals, $C_1$–$C_4$ alkoxy radicals and halogen atoms, wherein said halogen atoms are chosen from chlorine, bromine and fluorine;
it being understood that, when n=2, when $R_1$ represents a mesyl radical, when $R_3$ represents a methyl radical in the 6 position and when $R_2$ represents an $NHR_4$ group, then $R_4$ is other than a hydrogen atom.

2. The composition of claim 1, wherein said keratinous fibers are human keratinous fibers.

3. The composition of claim 2, wherein said human keratinous fibers are hair.

4. The composition of claim 1, wherein said acid addition salts are chosen from hydrochlorides, hydrobromides, sulphates and tartrates.

5. The composition of claim 1, wherein said para-phenylenediamines are chosen from 2-(β-mesylaminoethyloxy)-para-phenylenediamine, 2-(β-ureidoethyloxy)-para-phenylenediamine, 2-(β-acetylaminoethyloxy)-para-phenylenediamine, and 2-(β-aminoethyloxy)-para-phenylenediamine, and acid addition salts thereof.

6. The composition of claim 1, wherein said at least one coupler is chosen from meta-aminophenol, 5-amino-2-methoxyphenol, 5-amino-2-(β-hydroxyethyloxy)phenol, 5-amino-2-methylphenol, 5-N-(β-hydroxyethyl)amino-2-methylphenol, 5-N-(γ-hydroxypropyl)amino-2-methylphenol, 1,3-dihydroxybenzene, 2-methyl-1,3-dihydroxybenzene, 4-chloro-1,3-dihydroxybenzene and acid addition salts thereof.

7. The composition of claim 1, wherein said at least one oxidation base represents from 0.0005 to 10% by weight of the total weight of the dyeing composition.

8. The composition of claim 7, wherein said at least one oxidation base represents from 0.05 to 7% by weight of the total weight of the dyeing composition.

9. The composition of claim 1, wherein said at least one coupler represents from 0.0001 to 5% by weight relative to the total weight of the dyeing composition.

10. The composition of claim 9, wherein said at least one coupler represents from 0.005 to 3% by weight relative to the total weight of the dyeing composition.

11. The composition of claim 1, wherein said medium appropriate for dyeing comprises water or a mixture of water and at least one organic solvent chosen from $C_1$–$C_4$ alkanols, glycerol, glycols and glycol ethers, and aromatic alcohols.

12. The composition of claim 11, wherein said at least one organic solvent is present in a proportion ranging from 1 to 40% by weight approximately relative to the total weight of the dye composition.

13. The composition of claim 12, wherein said at least one organic solvent is present in a proportion ranging from 5 to 30% by weight approximately relative to the total weight of the dye composition.

14. The composition of claim 1, wherein said composition has a pH ranging from 5 to 12 approximately.

15. The composition of claim 14, wherein said pH ranges from 5 to 11.

16. The composition of claim 1, wherein said composition further comprises at least one additional ingredient chosen from
oxidation bases other said at least one oxidation base of claim 1, couplers other than said at least one coupler of claim 1 and direct dyes.

17. The composition of claim 1, wherein said composition additionally contains at least one adjuvant chosen from anionic, cationic, nonionic and amphoteric surfactants, anionic, cationic, nonionic and amphoteric polymers, organic and inorganic thickeners, antioxidants, penetration agents, sequestrants, fragrances, buffers, dispersants, conditioners, film forming agents, preserving agents and opacifiers.

18. The composition of claim 1, wherein said composition is in the form of a liquid, a cream, a gel or any other form appropriate for dyeing keratinous fibers.

19. A method for dyeing keratinous fibres, comprising the steps of contacting said fibres for a time sufficient to achieve color development, with a dye composition comprising, in a medium appropriate for dyeing:
at least one oxidation base chosen from para-phenylenediamines of formula (I) and acid addition salts thereof:

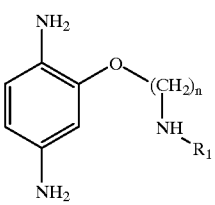

(I)

in which:
R₁ is chosen from a hydrogen atom, mesyl radicals, carbamoyl radicals, and acetyl radicals,
n is an integer ranging from 1 to 4; and
at least one coupler chosen from compounds of formula (II) and acid addition salts thereof;

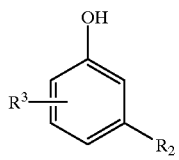

(II)

in which:
- $R_2$ is chosen from a hydroxyl radical and $NHR_4$ groups where $R_4$ is chosen from a hydrogen atom, $C_1$–$C_4$ alkyl radicals, $C_1$–$C_4$ monohydroxyalkyl radicals, and $C_2$–$C_4$ polyhydroxyalkyl radicals,
- $R_3$ is chosen from a hydrogen atom, $C_1$–$C_4$ alkyl radicals, $C_1$–$C_4$ alkoxy radicals and halogen atoms, wherein said halogen atoms are chosen from chlorine, bromine and fluorine;
- it being understood that, when n=2, when $R_1$ represents a mesyl radical, when $R_3$ represents a methyl radical in the 6 position and when $R_2$ represents an $NHR_4$ group, then $R_4$ is other than a hydrogen atom.

20. The method of claim 19, wherein said keratinous fibers are human keratin fibers.

21. The method of claim 20, wherein said human keratinous fibers are hair.

22. The method of claim 19, wherein said dye composition is mixed at the time of said contacting with an oxidizing composition comprising, in a medium suitable for dyeing, at least one oxidizing agent present in an amount sufficient for color development.

23. The method of claim 19, wherein said time sufficient ranges from 3 to 40 minutes.

24. The method of claim 23, wherein said time sufficient ranges from 5 to 30 minutes.

25. The method of claim 22, wherein said at least one oxidizing agent is chosen from hydrogen peroxide, urea peroxide, alkali metal bromates and persalts.

26. The method of claim 22, wherein said oxidizing composition including the oxidizing agent after mixing with the dyeing composition has a pH ranging from 2 to 12.

27. The method of claim 26, wherein said pH ranges from 5 to 11.

28. The method of claim 19, wherein wherein an oxidizing composition is contacted with said keratin fibers simultaneously or sequentially with said dye composition.

29. The method of claim 19, wherein an oxidizing composition is contacted with said keratin fibers separately from said dye composition.

30. The method of claim 22, wherein said oxidizing composition additionally contains at least one adjuvant chosen from anionic, cationic, nonionic and amphoteric surfactants, anionic, cationic, nonionic and amphoteric polymers, organic and inorganic thickeners, antioxidants, penetration agents, sequestrants, fragrances, buffers, dispersants, conditioners, film forming agents, preserving agents and opacifiers.

31. The composition of claim 1, wherein said composition further comprises an oxidizing composition comprising, in a medium appropriate for dyeing, at least one oxidizing agent present in an amount sufficient for color development of said keratinous fibers.

32. The composition of claim 31, wherein said oxidizing agent is chosen from hydrogen peroxide, urea peroxide, alkali metal bromates and persalts.

33. The composition of claim 31, wherein the pH of said oxidizing composition including the oxidizing agent after mixing with said dyeing composition ranges from 2 to 12.

34. The composition of claim 33, wherein said pH ranges from 5 to 11.

35. The composition of claim 31, wherein said oxidizing composition additionally contains at least one adjuvant chosen from anionic, cationic, nonionic and amphoteric surfactants, anionic, cationic, nonionic and amphoteric polymers, organic and inorganic thickeners, antioxidants, penetration agents, sequestrants, fragrances, buffers, dispersants, conditioners, film forming agents, preserving agents and opacifiers.

36. The compositions of claim 31, wherein said composition which is finally applied to keratinous fibres is in the form of a liquid, a cream, a gel, or any other form appropriate for carrying out dyeing of keratinous fibres.

37. A multi-compartment dyeing device or kit for dyeing keratin fibers, comprising at least two compartments, wherein
- a first compartment contains a dyeing composition, in a medium appropriate for dyeing, comprising:
  - at least one oxidation base chosen from para-phenylenediamines of formula (I) and acid addition salts thereof:

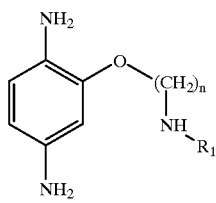

(I)

in which:
- $R_1$ is chosen from a hydrogen atom, mesyl radicals, carbamoyl radicals, and acetyl radicals,
- n is an integer ranging from 1 to 4; and
- at least one coupler chosen from compounds of formula (II) and acid addition salts thereof:

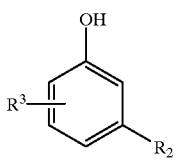

(II)

in which:
- $R_2$ is chosen from a hydroxyl radical and $NHR_4$ groups where $R_4$ is chosen from a hydrogen atom, $C_1$–$C_4$ alkyl radicals, $C_1$–$C_4$ monohydroxyalkyl radicals, and $C_2$–$C_4$ polyhydroxyalkyl radicals,
- $R_3$ is chosen from a hydrogen atom, $C_1$–$C_4$ alkyl radicals, $C_1$–$C_4$ alkoxy radicals and halogen atoms, wherein said halogen atoms are chosen from chlorine, bromine and fluorine;
- it being understood that, when n=2, when $R_1$ represents a mesyl radical, when $R_3$ represents a methyl radical in the 6 position and when $R_2$ represents an $NHR_4$ group, then $R_4$ is other than a hydrogen atom; and
- a second compartment contains an oxidizing composition.

* * * * *

UNITED STATES PATENT AND TRADEMARK OFFICE
CERTIFICATE OF CORRECTION

PATENT NO.    : 6,440,176 B2                                    Page 1 of 1
DATED         : August 27, 2002
INVENTOR(S)   : Marie-Pascale Audousset et al.

It is certified that error appears in the above-identified patent and that said Letters Patent is hereby corrected as shown below:

<u>Title page,</u>
Item [75], Inventors, "Asniéres" should read -- Asnières --.
Item [57], ABSTRACT,
Line 2, insert -- , in particular of human keratinous fibers, -- before "such".
Line 2, "comprises" should read -- comprising --.

<u>Column 9,</u>
Line 54, after "phenylenediamine" delete the comma.
Line 66, "of" should read -- relative to --.

<u>Column 10,</u>
Line 2, "of" should read -- relative to --.
Line 29, after "other" insert -- than --.
Line 67, "thereof;" should read -- thereof: --.

<u>Column 11,</u>
Line 4, "keratin" should read -- keratinous --.
Line 43, delete the second occurrence of "wherein".

<u>Column 12,</u>
Line 11, "compositions" should read -- composition --.

Signed and Sealed this

Fourth Day of January, 2003

JAMES E. ROGAN
*Director of the United States Patent and Trademark Office*